(12) United States Patent
Rhee et al.

(10) Patent No.: US 11,642,015 B2
(45) Date of Patent: May 9, 2023

(54) ENDOSCOPE AND SINUS ENTERING ENDOSCOPE

(71) Applicant: SEOUL NATIONAL UNIVERSITY HOSPITAL, Seoul (KR)

(72) Inventors: Chae Seo Rhee, Yongin (KR); Sung Woo Cho, Seoul (KR)

(73) Assignee: SEOUL NATIONAL UNIVERSITY HOSPITAL, Seoul (KR)

( * ) Notice: Subject to any disclaimer, the term of this patent is extended or adjusted under 35 U.S.C. 154(b) by 339 days.

(21) Appl. No.: 17/042,048

(22) PCT Filed: Feb. 25, 2019

(86) PCT No.: PCT/KR2019/002279
§ 371 (c)(1),
(2) Date: Sep. 25, 2020

(87) PCT Pub. No.: WO2019/190061
PCT Pub. Date: Oct. 3, 2019

(65) Prior Publication Data
US 2021/0076925 A1    Mar. 18, 2021

(30) Foreign Application Priority Data

Mar. 26, 2018    (KR) .................. 10-2018-0034405

(51) Int. Cl.
*A61B 1/018*    (2006.01)
*A61B 1/00*     (2006.01)
(Continued)

(52) U.S. Cl.
CPC ............ *A61B 1/018* (2013.01); *A61B 1/0051* (2013.01); *A61B 1/00071* (2013.01); *A61B 1/044* (2022.02); *A61B 1/233* (2013.01)

(58) Field of Classification Search
CPC ... A61B 1/233; A61B 1/00071; A61B 1/0051; A61B 1/04; A61B 1/00; A61B 1/005;
(Continued)

(56) References Cited

U.S. PATENT DOCUMENTS

2005/0267400 A1    12/2005  Haarala et al.
2007/0276180 A1*   11/2007  Greenburg ......... A61B 1/00147
                                                    600/106
(Continued)

FOREIGN PATENT DOCUMENTS

JP    2007-521926 A    8/2007
JP    2015-524289 A    8/2015
(Continued)

OTHER PUBLICATIONS

Search Report for International Application No. PCT/KR2019/002279, dated May 22, 2019.
(Continued)

*Primary Examiner* — Timothy J Neal
*Assistant Examiner* — James Edward Boice (57) ABSTRACT

A sinus entering endoscope according to an embodiment of the present invention comprises: a body including a plurality of operation parts; an insertion part extending from the front end of the body to be inserted into the sinus through the nasal cavity, and having at least one working channel; and an applicator load part which is disposed in the body and on which a plurality of applicators which can selectively enter through the working channel can be mounted.

8 Claims, 11 Drawing Sheets

(51) Int. Cl.
*A61B 1/005* (2006.01)
*A61B 1/233* (2006.01)
*A61B 1/04* (2006.01)

(58) Field of Classification Search
CPC .......... A61B 1/018; A61B 2017/00225; A61B 17/00234; A61B 1/00119; A61M 3/00
USPC ........................................................ 600/104
See application file for complete search history.

(56) References Cited

U.S. PATENT DOCUMENTS

| | | | |
|---|---|---|---|
| 2007/0299305 A1* | 12/2007 | Murakami | A61B 1/00133 606/1 |
| 2008/0058595 A1 | 3/2008 | Snoke et al. | |
| 2010/0099946 A1 | 4/2010 | Jenkins et al. | |
| 2011/0152878 A1* | 6/2011 | Trusty | A61B 1/00154 606/130 |
| 2012/0071856 A1 | 3/2012 | Goldfarb et al. | |
| 2012/0123208 A1* | 5/2012 | Remmerswaal | A61M 16/0875 600/116 |
| 2014/0012075 A1* | 1/2014 | Konstorum | A61B 1/0057 600/104 |
| 2014/0100424 A1* | 4/2014 | Hoshino | A61B 1/00002 600/118 |
| 2015/0196735 A1 | 7/2015 | Olig et al. | |
| 2015/0342445 A1* | 12/2015 | Jones | A61B 1/00133 600/106 |
| 2017/0035277 A1* | 2/2017 | Kucharski | A61B 1/012 |
| 2017/0095239 A1* | 4/2017 | Smith | A61B 1/00133 |

FOREIGN PATENT DOCUMENTS

| | | |
|---|---|---|
| KR | 20110056409 A | 5/2011 |
| KR | 20130107304 A | 10/2013 |
| KR | 101376374 B1 | 3/2014 |
| KR | 20160130776 A | 11/2016 |
| WO | WO2014156286 A1 | 10/2014 |
| WO | WO2015123313 A1 | 8/2015 |

OTHER PUBLICATIONS

Extended European Search Report for Application No. 19776144.8, dated Nov. 23, 2021.

* cited by examiner

ENDOSCOPE AND SINUS ENTERING ENDOSCOPE

CROSS-REFERENCE TO RELATED APPLICATION

This application is a National Phase of International Application No. PCT/KR2019/002279, filed on Feb. 25, 2019, which claims priority to Korean Patent Application No. 10-2018-0034405, filed on Mar. 26, 2018, in the Korean Intellectual Property Office, the disclosures of each of which are incorporated herein by reference.

TECHNICAL FIELD

The present disclosure relates to an endoscope, and more specifically, to an endoscope which can also be used for the treatment of sinusitis.

BACKGROUND ART

Chronic sinusitis is a common disease that occurs in 8.6% of the Korean population. Functional endoscopic sinus surgery performed during the surgical treatment of chronic rhinosinusitis requires general anesthesia in most cases and, although rare, can cause serious complications such as orbital complications and cerebral hemorrhage.

In addition, since it damages the surrounding tissues during surgery, there is pain after surgery and the recovery rate is slow. To solve these problems, a surgical method was developed to open the natural sinus cavity while minimizing damage to the surrounding structures by inserting a small balloon catheter into the nasal cavity. This method has advantages in that it allows local anesthesia, has a short recovery time, has a low complication rate, enables simple postoperative management, etc.

Two main types of devices are currently used for the insertion of the balloon catheter.

One type of device employs a method to use a guide wire provided with a luminescent lamp. Since natural sinus cavities are located being hidden in the uncinate process and the ethmoidal sinus, it is normally not possible to directly check natural cavities using only an upright endoscope. Accordingly, it is required that a guide wire be inserted into the entrance of the sinus under the guidance of an endoscope, and then, the front end of the guide wire be inserted through the natural cavities by repeatedly moving the guide wire forward and backward to the natural cavities, relying on the touch sense without checking with the naked eye considering the anatomical position and direction of the natural cavities. Once it is determined that the front end of the guide wire has been inserted into the natural cavities, it is required to check the luminous position of the guide wire around the opening and outside of the face, and then check whether the guide wire has entered the maxillary sinus or the frontal sinus, and the balloon catheter be inserted thereinto along the guide wire. However, the above method is a method where the guide wire is inserted while only checking the luminous position from the outside without checking the internal structures of the nasal cavity and sinuses, it is possible that the method may damage the surrounding tissues or structures.

The other type of device is a device that indirectly checks whether an invader has been inserted into the sinus using a separate navigation device. This type of device requires expensive navigation device, and it is possible that the device may damage surrounding tissues or structures of the nasal cavities or the sinuses due to errors in the navigation device.

DISCLOSURE

Technical Problem

An object of the present invention is to provide an endoscope which can check in real time the internal images of the nasal cavity and the sinuses and into which applicators such as a guide wire can be inserted.

Additionally, another object of the present invention is to provide an endoscope which can insert a plurality of applicators into a surgical site more easily and rapidly.

The objects of the present invention are not limited to those described above, and other objects not describe will be clearly understood by those skilled in the art from the description shown below.

Technical Solution

In order to achieve the above objects, a paranasal sinus entering endoscope according to an embodiment of the present invention includes: a body, which includes a plurality of operation parts; an insertion part, which is extending from the front end of the body to be inserted into the paranasal sinus through the nasal cavity, and having at least one working channel; and an applicator load part, which is disposed in the body and on which a plurality of applicators that can selectively enter through the working channel can be mounted.

In order to achieve the above objects, a paranasal sinus entering endoscope according to an embodiment of the present invention includes: a body, which includes a plurality of operation parts; a rigid part, which is extending from the front end of the body to be inserted into the nasal cavity; a flexible part, which is extending from the rigid part and formed to be bent and inserted into the paranasal sinus on the front end; an image acquiring unit, which is disposed at the front end of the flexible part and acquires the image of the front of the flexible part; and a bending operation part, which allows the flexible part to be bent by a user's operation.

In order to achieve the above objects, an endoscope according to an embodiment of the present invention includes: a body, which includes a plurality of operation parts; an insertion part, which is extending from the front end of the body to be inserted into the body of a patient, and having at least one working channel; and an applicator load part, which is configured to mount a plurality of applicators, is disposed to the body to be able to rotate, and arrange the mounted plurality of applicators in the working channel according to the rotation angle.

Other specific subject matters of the present invention are included in the detailed description and drawings.

Advantageous Effects

According to embodiments of the present invention, the present invention has at least the following effects.

Since applicators such as a guide wire can be inserted while checking in real time the internal images of the nasal cavity and the sinuses, the surgery can be performed more safely.

Since a plurality of applicators can be inserted into the surgical site more easily and rapidly, the convenience of surgery can be improved and the time required for surgery can be reduced.

The effects according to the present invention are not limited by the details illustrated above, and more various effects are included in the present specification.

MODE FOR DISCLOSURE

Advantages and features of the present invention and a method of achieving them will become apparent with reference to embodiments described later in detail together with the accompanying drawings. However, the present invention is not limited to these embodiments disclosed below, but may be implemented in various different forms. Only these embodiments are provided to complete the disclosure of the present invention and to fully inform the scope of the invention to those skilled in the art to which the present invention belongs. The present invention is only defined by the scope of the claims. The same reference numerals refer to the same components throughout the specification.

In addition, embodiments described in the present specification will be described with reference to sectional views and/or schematic diagrams which are ideal exemplary diagrams of the present invention. Therefore, the shape of the exemplary diagram may be modified by manufacturing technology and/or permissible errors. In addition, in each of the drawings shown in the present invention, each component may be somewhat enlarged or reduced in consideration of convenience of description. The same reference numerals refer to the same components throughout the specification.

Hereinafter, the present invention will be described with reference to the drawings for explaining a treatment device according to an embodiment of the present invention.

Figure 1:
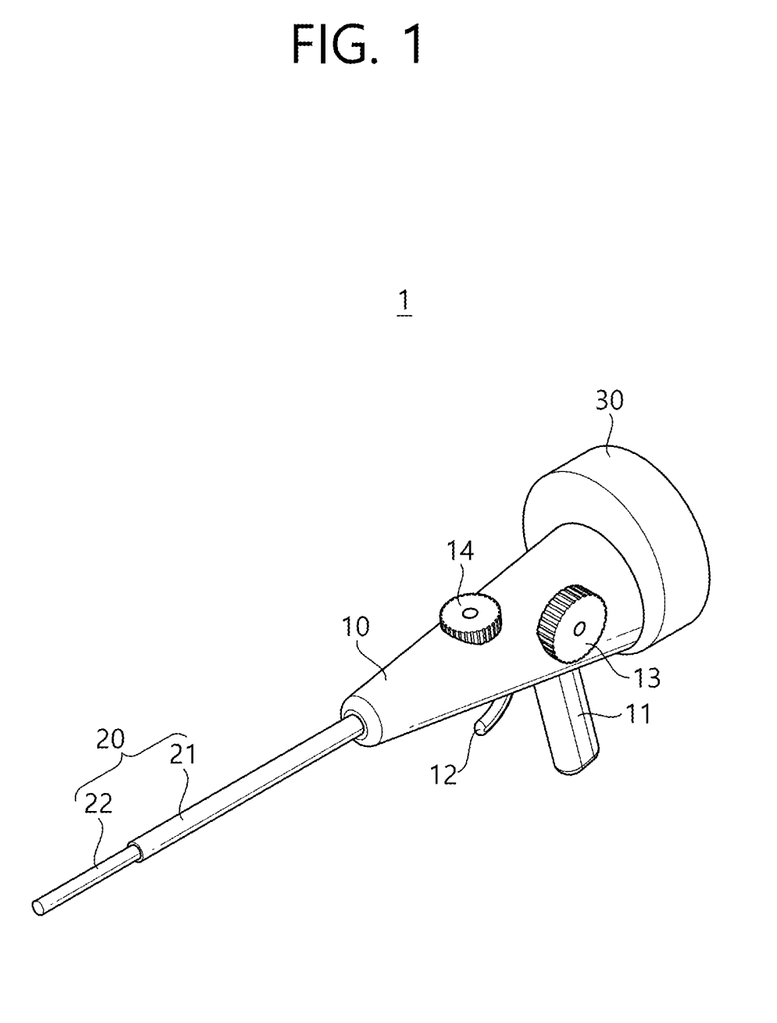
FIG. 1 is a perspective view showing an endoscope according to an embodiment of the present invention.

FIG. 1 is a perspective view showing an endoscope according to an embodiment of the present invention.

As shown in FIG. 1, the endoscope 1 according to an embodiment of the present invention includes a body 10, an insertion part 20, and an applicator load part 30. The insertion part 20 can be extended from the front end of body 10, and the applicator load part 30 can be rotatably mounted at the rear end of body 10.

The body 10 has a handle 11, an operation unit for selecting an applicator 12, a bending operation part 13, and an operation unit for moving an applicator 14.

The handle 11 is a configuration that a user (e.g., a doctor, etc.) who operates the endoscope 1 grips by hand.

The operation unit for selecting an applicator 12 is configured to operate the applicator load part 30, and can be formed in a structure similar to the trigger in front of the handle 11.

A bending operation part 13 is a configuration that operates the bending direction of a flexible part 22 of an insertion part 20, and can be disposed on one side of the body 10. The endoscope 1 according to the embodiment shown in FIG. 1 shows a model in which the user can operate the bending operation part 13 with the thumb of the right hand while holding the handle 11 with the right hand. According to an embodiment, the bending operation part 13 may also be configured to be arranged on the opposite side so that the user can operate the bending operation part 13 with the thumb of the left hand while holding the handle 11 with the left hand.

The movement of the applicator according to the operation of the bending operation part 13 will be described later.

The operation unit for moving an applicator 14 is a configuration in which the applicators are operated to move forward or backward along the inside of the insertion part 20, and may be disposed on top portion of the body 10. A user can operate the operation unit for moving an applicator 14 with the other hand while holding the handle 11 with any of the two hands. FIG. 1 shows a configuration in which the operation unit for moving an applicator 14 is disposed above the body 10, but the position of the operation unit for moving an applicator 14 may vary according to embodiments. For example, the operation unit for moving an applicator 14 may be located in front of or opposite to the bending operation part 13.

As shown in FIG. 1, the insertion part 20 includes a rigid part 21 and a flexible part 22.

The rigid part 21 extends forward from the front end of body 10, and the flexible part 22 extends from the front end of the rigid part 21.

As described above, the flexible part 22 is formed of a structure or material that can easily be bent in at least two directions. In contrast, the rigid part 21 is formed of a rigid structure or material that is not easily bent compared to the flexible part 22.

Figure 2:
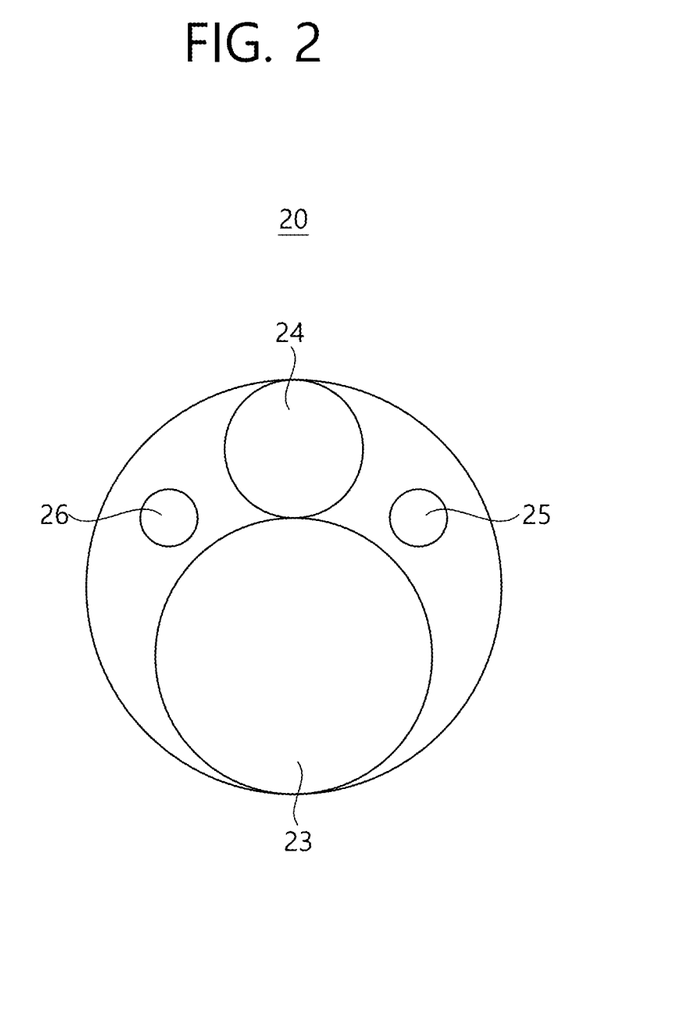
FIG. 2 is a schematic diagram illustrating a front end of an insertion part of an endoscope according to an embodiment of the present invention.

FIG. 2 is a schematic diagram illustrating a front end of an insertion part of an endoscope according to an embodiment of the present invention.

As shown in FIG. 2, the insertion part 20 includes a working channel 23 and image acquiring units (24, 25, and 26).

The working channel 23 is a channel through which the applicator (a guide wire, a balloon catheter, a stent catheter, a tube, etc.), which enters through the endoscope 1, passes.

The image acquiring units (24, 25, and 26) are units that acquire the internal images of the body through the front end of the flexible part 22, and they include a lens 24, a light source 25, and a cable 26.

The lens 24 and the light source 25 are disposed in front of the flexible part 22. The light source 25 provides illumination to the front direction of the flexible part 22, and the cable 26 provides the power supplied by the light source 25. The lens 24 can prevent the formation of frost on the surface by hydrophobic treatment.

The cable 26 and the working channel 23 extend through the flexible part 22 and the rigid part 21 up to the body 10.

Although not shown, the image acquiring units (24, 25, and 26) may include an optical cable which extends from the rear end of the lens 24 to the outside of the endoscope 1. An image sensor, etc. may come into contact with the end of the optical cable so as to convert optical information transmitted through the optical cable into an image.

Although not shown, the image acquiring units (24, 25, and 26) may include a small camera instead of an optical cable. In this case, the image information captured by the small camera may be transmitted to the outside of the endoscope 1 as an electrical signal.

Figure 3:
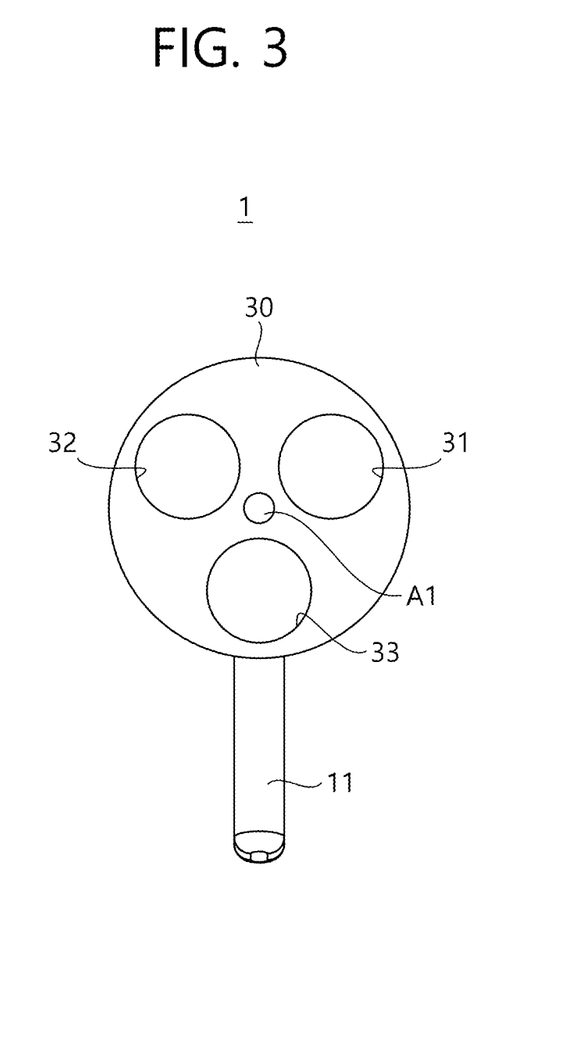
FIG. 3 is a schematic diagram showing an applicator load part of an endoscope according to an embodiment of the present invention.
Figure 4:
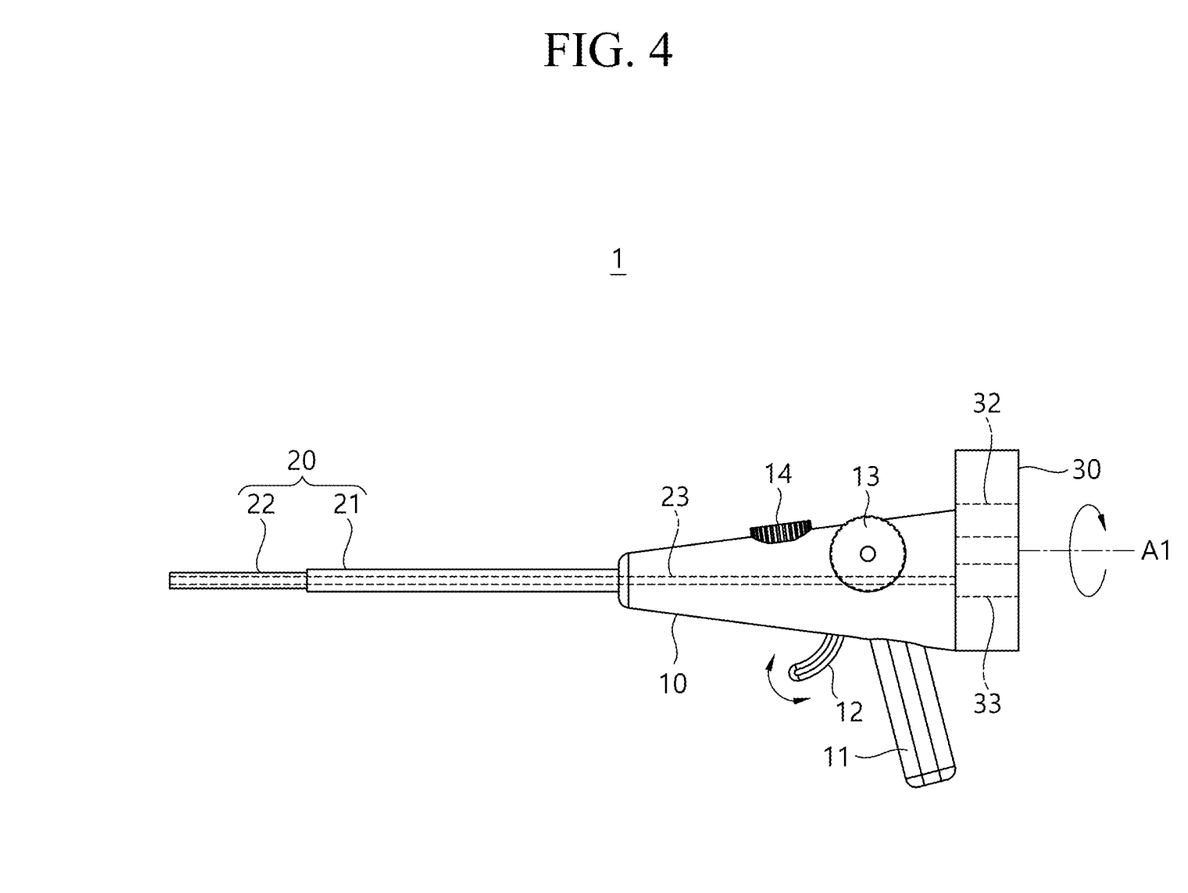
FIG. 4 is a perspective view showing an endoscope according to an embodiment of the present invention for explaining the positional relationship between the working channel of the endoscope and the loading hole of the applicator load part.

FIG. 3 is a schematic diagram showing an applicator load part of an endoscope according to an embodiment of the present invention; and FIG. 4 is a perspective view showing an endoscope according to an embodiment of the present invention for explaining the positional relationship between the working channel of the endoscope and the loading hole of the applicator load part.

As shown in FIGS. 1 and 3, the applicator load part 30 is disposed to be rotatable about the rotation shaft (A1) at the rear end of the body 10.

The applicator load part 30 includes a plurality of loading holes (31, 32, and 33) arranged radially around the rotation axis (A1). Each of the loading holes (31, 32, and 33) may be formed to have the same distance from the rotation shaft A1.

The applicator that will enter the body through an endoscope 1 is mounted on each loading hole (31, 32, and 33). Details on this will be described later.

As shown in FIG. 4, the working channel 23 is extended from the front end of the flexible part 22 up to the applicator load part 30 through the flexible part 22, the rigid part 21, and the body 10.

Additionally, one of the loading holes (31, 32, and 33) of the applicator load part 30 is located coaxially with the working channel 23. Accordingly, the applicator coaxially mounted in the loading hole 33 (refer to FIG. 4) with the working channel 23 can enter the working channel 23.

As shown in FIG. 4, the applicator load part 30 may be configured to rotate by a predetermined angle with respect to the rotation shaft (A1) by the operation unit for selecting an applicator 12 is pulled.

Therefore, the user can select the applicator to be inserted through the working channel 23 by rotating the applicator load part 30 by simply pulling the operation unit for selecting an applicator 12 while holding the handle 11.

Therefore, when a plurality of applicators are used for surgery, treatment, etc. using the endoscope 1, the user can allow the applicators to be inserted through the working channel 23 by pulling the operation unit for selecting an applicator 12 so that the required applicator is positioned coaxially with the working channel 23, if necessary, with the plurality of applicators mounted on the loading holes (31, 32, and 33) of the applicator load part 30, respectively.

Accordingly, the user convenience can be improved, and the time required for the surgery/treatment process can be reduced.

Figure 5:
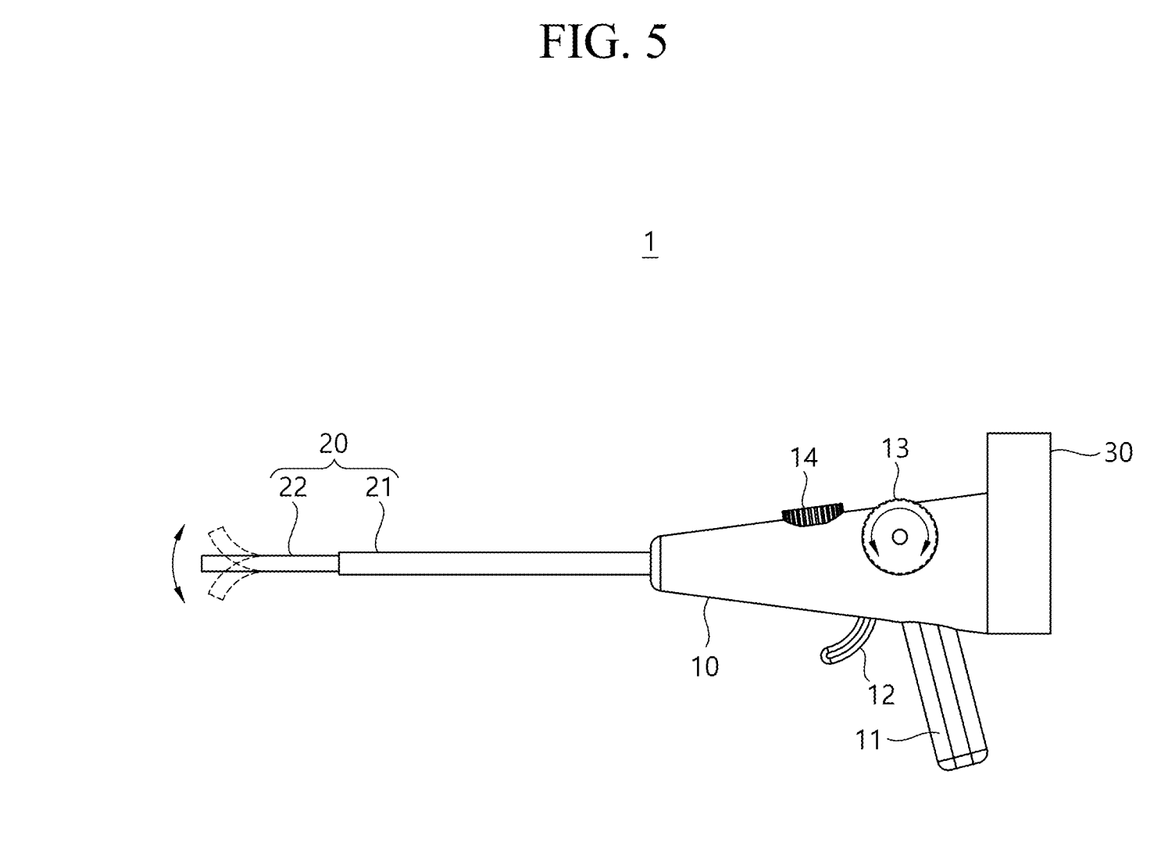
FIG. 5 is a schematic diagram for explaining the operation of a bending operation part of an endoscope according to an embodiment of the present invention.

FIG. 5 is a schematic diagram for explaining the operation of a bending operation part of an endoscope according to an embodiment of the present invention.

As shown in FIG. 5, the flexible part 22 is configured to be bent in a first direction or a second direction as the bending operation part 13 rotates clockwise or counterclockwise.

For example, the flexible part 22 may be configured so that a clockwise rotation of the bending operation part 13 allows the front end of the flexible part 22 to be bent to a first direction, whereas a counterclockwise rotation of the bending operation part 13 allows the front end of the flexible part 22 to be bent to a second direction.

The first direction and the second direction may be horizontal or vertical directions, respectively.

Figure 6:
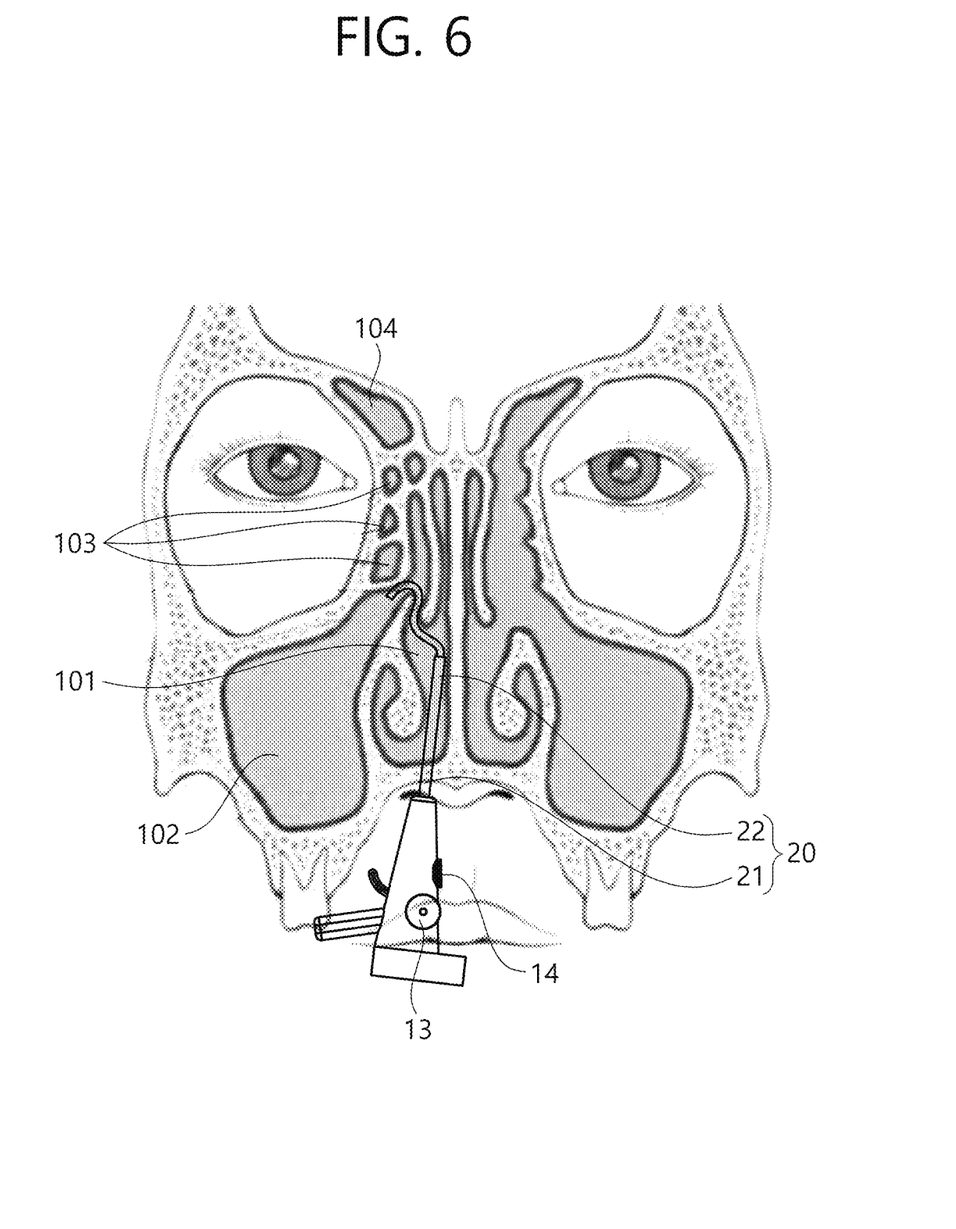
FIG. 6 is a schematic diagram for explaining a method of using an endoscope according to an embodiment of the present invention for the treatment of sinusitis.

FIG. 6 is a schematic diagram for explaining a method of using an endoscope according to an embodiment of the present invention for the treatment of sinusitis.

As shown in FIG. 6, the endoscope 1 according to an embodiment of the present invention may be used to be inserted into the sinus for the treatment of sinusitis.

Sinus refers to the empty space in the facial bone, which is connected to the nasal cavity 101. The sinus includes a maxillary sinus 102 (which is the internal space of both cheeks), an ethmoidal sinus 103 (which is the internal space of the nasal bone between the eyes), and a sphenoidal sinus (which is not shown in FIG. 6, but is located deep inside both eyes).

Sinusitis refers to the occurrence of inflammation caused by the penetration of bacteria or viruses into the sinuses, and it often occurs in the maxillary sinus 102 even within the sinuses.

When the endoscope 1 according to an embodiment of the present invention is used for the treatment of sinusitis, as shown in FIG. 6, the user inserts the insertion part 20 into the nasal cavity 101.

Since the insertion part 20 includes the rigid part 21 extending from the front end of body 10, the insertion part 20 can easily be inserted a certain depth from the nostril, the entrance of the nasal cavity 101.

The path from the nasal cavity 101 to the maxillary sinus 102, the ethmoidal sinus 103, and the frontal sinus 104 is not a straight line. Therefore, the rigid part 21 can no longer enter, and the flexible part 22 must be bent to be inserted into the maxillary sinus 102, the ethmoidal sinus 103, the frontal sinus 104, etc.

Since the endoscope 1 according to an embodiment of the present invention includes image acquiring units (24, 25, and 26), which include a lens 24, a light source 25, etc. on the front end of the flexible part 22, the user should check the image information within the nasal cavity 101 and the sinuses being transmitted from image acquiring units (24, 25, and 26), bend the flexible part 22 using the bending operation part 13, allow the flexible part 22 to advance gradually, and thereby allow the front end of the flexible part 22 to be inserted into the internal space of the sinus.

FIG. 6 shows an example in which the flexible part 22 is inserted into the maxillary sinus 102.

Figure 7:
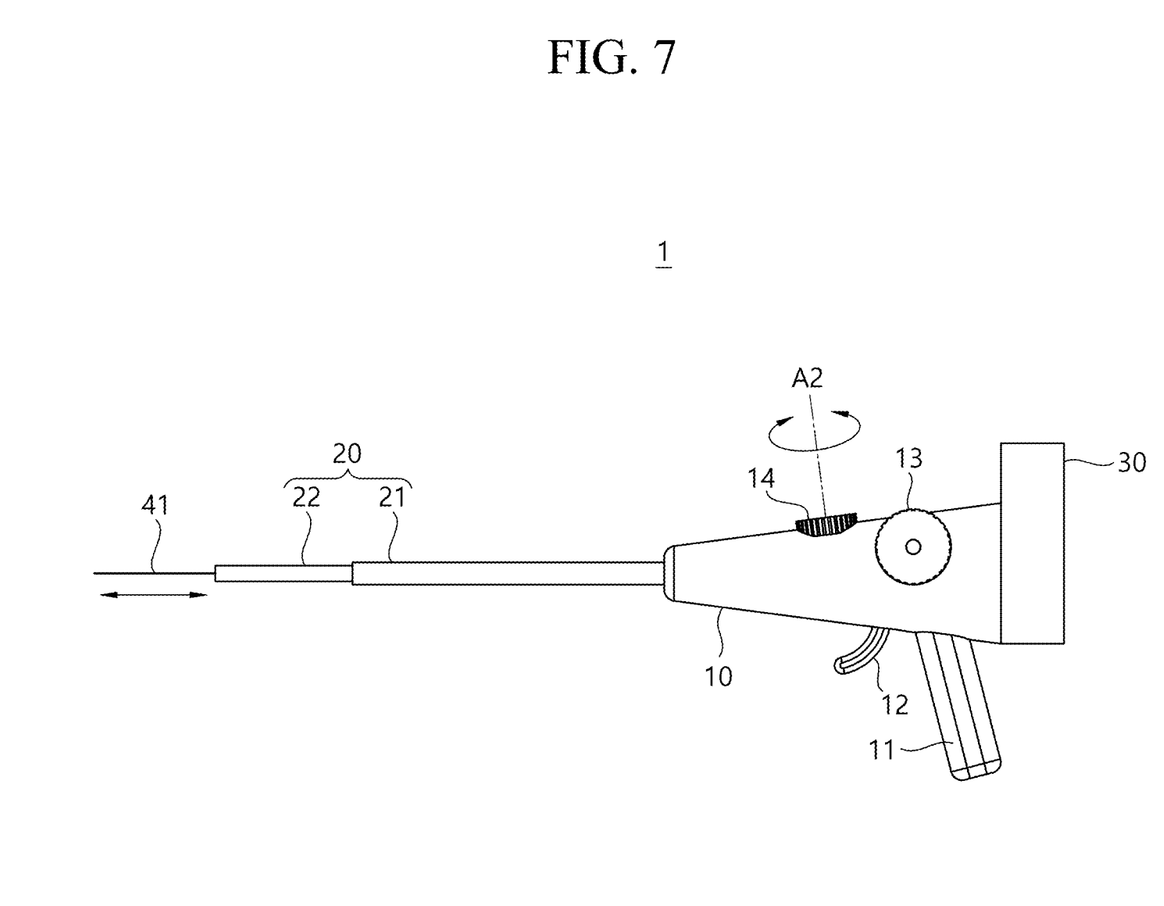
FIG. 7 is a schematic diagram for explaining the operation of an operation unit for moving an applicator of the endoscope according to an embodiment of the present invention.

FIG. 7 is a schematic diagram for explaining the operation of an operation unit for moving an applicator of the endoscope according to an embodiment of the present invention.

As shown in FIG. 7, the body 10 is configured such that when the operation unit for moving an applicator 14 is rotated around the axis of rotation (A2), the applicator 41 within the working channel 23 moves along the working channel 23.

For example, when the user rotates the operation unit for moving an applicator 14 clockwise, the applicator 41 advances along the working channel 23 and is exposed to the outside through the front end of the flexible part 22, whereas when the user rotates the operation unit for moving an applicator 14 counterclockwise, the applicator 41 can retreat along the working channel 23 and return to the body 10.

The applicator shown in FIG. 7 may be a guide wire 41.

According to an embodiment, the guide wire 41 may be used after being mounted on any one of the loading holes (31, 32, and 33) of the applicator load part 30 or may be used without being mounted on the applicator load part 30.

When the guide wire 41 is mounted on the applicator load part 30 and used, the guide wire 41 can optionally be used with other applicator(s) mounted on the applicator load part 30.

When the guide wire 41 is used without being mounted on the applicator load part 30, the guide wire 41 can be moved by the operation unit for moving an applicator 14 in a state being passed through the body 10. In this case, another applicator can be used with the guide wire.

After the user bends the flexible part 22 so that the front end of the flexible part 22 is positioned while advancing it toward the space where sinusitis has occurred (e.g., the maxillary sinus 102) or to be positioned within the space, and then, as shown in FIG. 7, the user can operate the operation unit for moving an applicator 14 to advance the guide wire 41 through the working channel 23, thereby allowing part of the guide wire 41 to be exposed through the front end of the flexible part 22.

As shown in FIG. 6, the path from the nasal cavity 101 to enter through the maxillary sinus 102, the ethmoidal sinus 103, and the frontal sinus 104 is rather narrow, and when sinusitis occurs, the path becomes narrower.

Therefore, when necessary, a space within the path through which the flexible part 22 or the applicator can enter must be provided.

Figure 8:
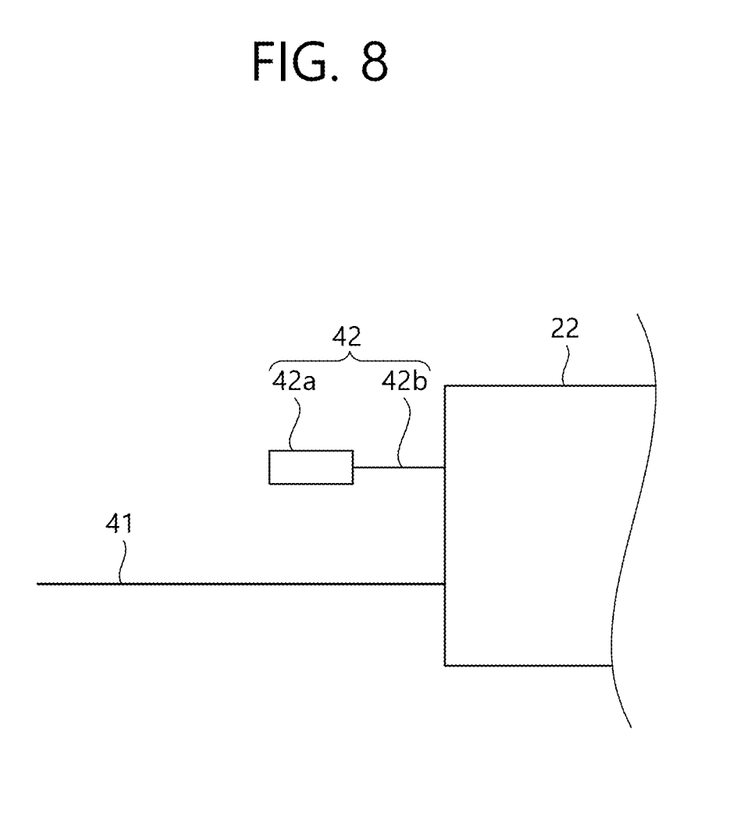
FIG. 8 is a schematic diagram for explaining an example of using a balloon catheter among applicators.

FIG. 8 is a schematic diagram for explaining an example of using a balloon catheter among applicators.

The balloon catheter 42 includes an inflatable balloon 42a and a wire 42b, in which a flow path to deliver air with the balloon 42a is formed. The wire 42b may be connected to a pump (not shown) that extends to the outside of the endoscope 1 and provides air supplied for the expansion of the balloon 42a.

The balloon catheter 42 may be in a state being mounted on any of the loading holes (31, 32, and 33) of the applicator load part 30. In this case, the user operates the operation unit for selecting an applicator 12 so that the loading holes (31, 32, and 33) where the balloon catheter 42 is mounted are coaxially located with the working channel 23, and operates the operation unit for moving an applicator 14 so that the balloon catheter 42 moves to the front end of the flexible part 22 through the working channel 23.

As shown in FIG. 8, the balloon catheter 42 may be configured to advance along the guide wire 41 within the working channel 23, in a state where the guide wire 41 is exposed to the front end of a flexible part 22 through the working channel 23.

The user can secure a space in such a manner that the user checks the image information transmitted from the image acquiring units (24, 25, and 26), operates the operation unit for moving an applicator 14 so that the balloon 42a of the balloon catheter 42 is positioned where a space needs to be secured, and then, allows the balloon 42a to be inflated.

Figure 9:
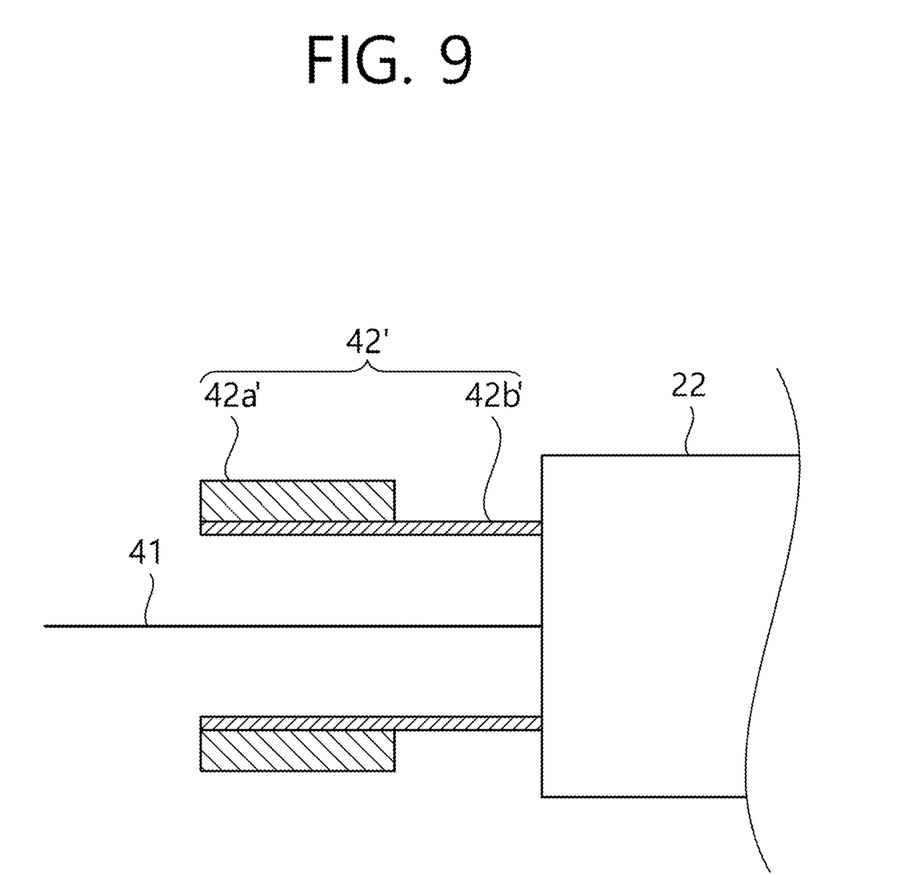
FIG. 9 is a schematic diagram showing a balloon catheter according to another embodiment.

FIG. 9 is a schematic diagram showing a balloon catheter according to another embodiment.

As shown in FIG. 9, the balloon catheter 42' according to another embodiment may be configured such that the guide wire 41 is received in the wire 42b'.

In this case, since the balloon catheter 42' can move along the guide wire 41 only by the advancement of the balloon catheter 42' by the operation of the operation unit for moving an applicator 14, the balloon catheter 42' can be more easily inserted into the sinuses.

Figure 10:
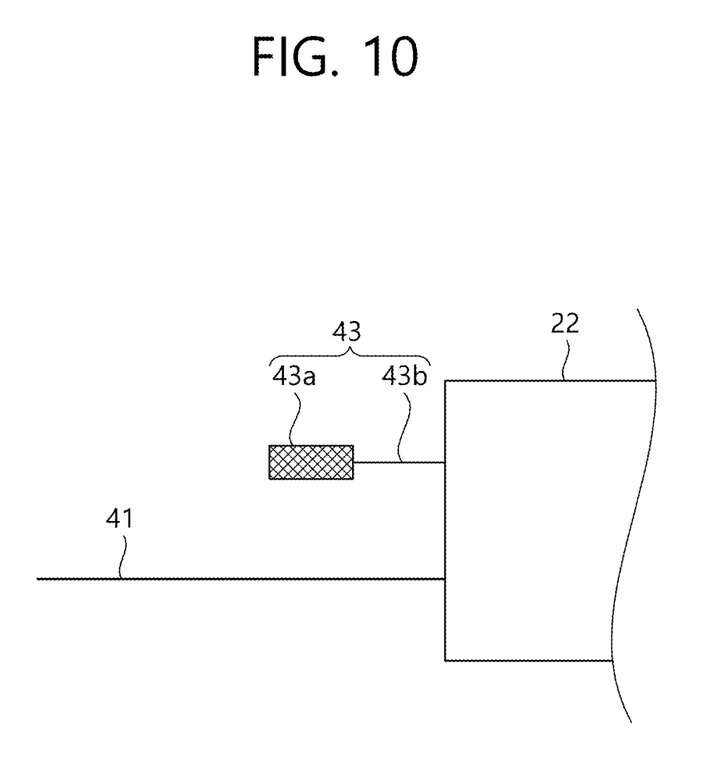
FIG. 10 is a schematic diagram for explaining an example of using a stent catheter among applicators.

FIG. 10 is a schematic diagram for explaining an example of using a stent catheter among applicators.

The stent catheter 43 includes a stent 43a and a stent cable 43b.

The stent 43a may be configured to have an inflatable structure, and the stent cable 43b may be configured to transmit power, signals, etc. to the stent 43a so as to inflate the stent 43a.

For example, the stent 43a may have a structure such that an inflatable balloon is included inside the stent 43a and the stent cable 43b may have a structure such that a flow path that supplies air to the balloon is included inside the stent cable 43b.

The stent catheter 43 may be in a state mounted on one of the loading holes (31, 32, and 33) of the applicator load part 30. In this case, the user operates the operation unit for selecting an applicator 12 so that the loading holes (31, 32, and 33), on which the stent catheter 43 is mounted, are coaxially located with the working channel 23, and operates the operation unit for moving an applicator 14 and allows the stent catheter 43 to move to the front end of the flexible part 22 through the working channel 23.

As shown in FIG. 10, the stent catheter 43 may be configured to advance along the guide wire 41 within the working channel 23 in a state where the guide wire 41 is exposed to the front end of the flexible part 22 through the working channel 23.

The user can mount the stent 43a in such a manner that the user checks the image information being transmitted from the image acquiring units (24, 25, and 26), operates the operation unit for moving an applicator 14 so that the stent 43a of the stent catheter 43 is located at the position where the stent 43a is to be mounted, and allows the stent 43a to be inflated.

The stent 43a may be installed to provide a space for the flexible part 22 or the applicator to pass through, or may be installed on the area of inflammation in a state where a drug is contained therein.

Although not shown, the stent catheter may also be configured such that the guide wire 41 is received within the stent cable 43b similar to the balloon catheter 42' shown in FIG. 9.

Figure 11:
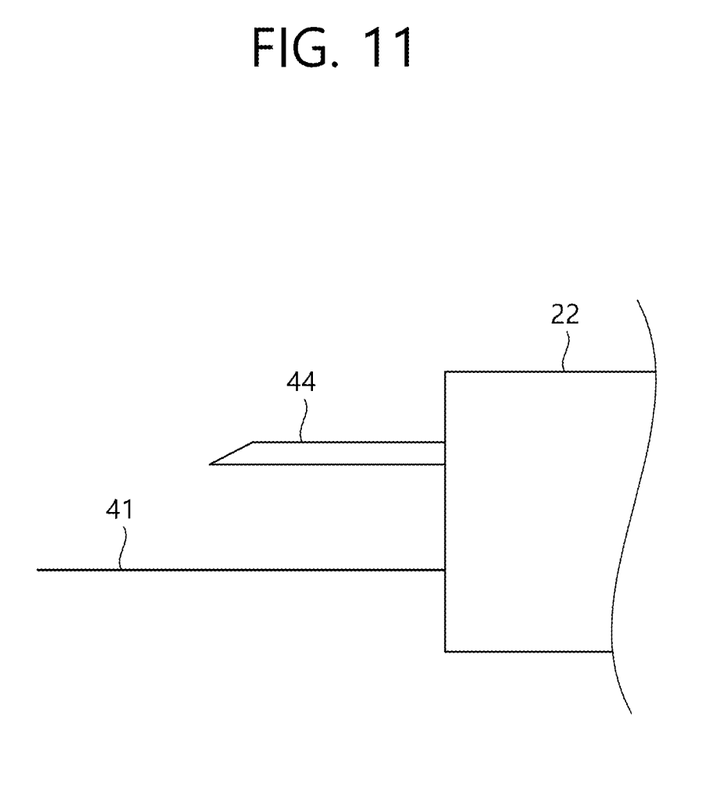
FIG. 11 is a schematic diagram for explaining an example of using a tube among applicators.

FIG. 11 is a schematic diagram for explaining an example of using a tube among applicators.

Tube 44 may also be used as an applicator of the endoscope 1 according to this embodiment.

The tube 44 may be in a state mounted on one of the loading holes (31, 32, and 33) of the applicator load part 30. In this case, the user operates the operation unit for selecting an applicator 12 so that the loading holes (31, 32, and 33), on which the tube 44 is mounted, are coaxially located with the working channel 23, and operates the operation unit for moving an applicator 14 and allows the flexible part 22 to move to the front end of the flexible part 22 through the working channel 23.

As shown in FIG. 11, the tube 44 may be configured to advance along the guide wire 41 within the working channel 23 in a state where the guide wire 41 is exposed to the front end of the flexible part 22 through the working channel 23.

The tube 44 can be used as a suction tube, a tube for spraying a washing solution/disinfectant/liquid drug, etc. As shown in FIG. 11, the front end of the tube 44 is formed sharply like a needle and thus the tube 44 may also be used like a syringe.

Although not shown, the tube may also be configured such that the guide wire 41 is received within the stent cable 43b similar to the balloon catheter 42' shown in FIG. 9.

As described above, the endoscope 1 according to an embodiment of the present invention is provided with image acquiring units (24, 25, and 26) on the front end of the flexible part 22. Therefore, when a guide wire, a balloon catheter, a stent catheter, a tube, etc. are inserted into the sinuses through the nasal cavity, the applicators can be inserted while visually checking the internal structures of the nasal cavity/sinuses, and thus, it is possible to safely insert the applicators without damaging the surrounding tissues or structures.

In particular, since the applicators are inserted while checking the internal structures of the nasal cavity/sinuses, even a novice can safely perform surgery and treatment.

In addition, the endoscope 1 according to an embodiment of the present invention is configured to mount a plurality of applicators required for a treatment process, and the user can select the applicator(s) to be inserted into the working channel 23 by simply operating the operation unit for selecting an applicator 12 provided in the endoscope 1, it is possible to reduce the user's convenience and the time required for the operation/treatment process.

In particular, in the case of the endoscope 1, where the working channel 23 must be composed of only one so as to insert it into a narrow space such as the sinus, the operation of selecting the applicator(s) to be inserted into the working channel 23 and the operation to advance and retreat the applicator(s) can both be performed in a state where a plurality of applicators are mounted thereon, the user convenience and the time required for surgery/treatment can be reduced.

Those of ordinary skill in the art to which the present invention pertains will appreciate that the present invention can be implemented in other specific forms without changing the technical spirit or essential features. Therefore, it should be understood that the embodiments described above are illustrative in all respects and not limiting. The scope of the present invention is indicated by the claims to be described later rather than the detailed description, and the meaning and scope of the claims and all the changes or modifications derived from the concept of equivalent should be interpreted as being included in the scope of the present invention.

Mode for Carrying Out the Invention

The sinus entering endoscope according to an embodiment of the present invention includes a body, which includes a plurality of operation parts; an insertion part, which is extending from the front end of the body to be inserted into the sinus through the nasal cavity, and having at least one working channel; and an applicator load part, which is disposed in the body and on which a plurality of applicators, that can selectively enter through the working channel, can be mounted The applicator load part can allow any one of a plurality of applicators to be positioned coaxially with the working channel.

The plurality of operation parts may include an operation unit for selecting an applicator, which locates any one of the plurality of applicators to be adjacent to an inlet of the channel by driving the applicator load part by a user's operation.

The applicator load part can allow the plurality of applicators to rotate around the axis of rotation according to the operation of the operation unit for selecting an applicator.

The plurality of operation parts may include an operation unit for moving an applicator, which allows the applicator, that has entered the working channel among the plurality of applicators, to move through the working channel by a user's operation.

The insertion part may include an image acquiring unit, which is disposed on the front end of the insertion part to acquire an image.

The insertion part may include a rigid part, which is extending from the front end of the body; and a flexible part, which is extending from the rigid part and formed to be bent, and wherein the plurality of operation parts include a bending operation part, which allows the flexible part to be bent by a user's operation The plurality of applicators may include at least one among a guide wire, a balloon catheter, and a stent catheter.

The sinus entering endoscope according to an embodiment of the present invention includes a body, which includes a plurality of operation parts; a rigid part, which is extending from the front end of the body to be inserted into the nasal cavity; a flexible part, which is extending from the rigid part and formed to be bent and inserted into the sinus on the front end; an image acquiring unit, which is disposed at the front end of the flexible part and acquires the image of the front of the flexible part; and a bending operation part, which allows the flexible part to be bent by a user's operation.

The sinus entering endoscope according to an embodiment of the present invention includes a body, which includes a plurality of operation parts; an insertion part, which is extending from the front end of the body to be inserted into the body of a patient, and having at least one working channel; and an applicator load part, which is configured to mount a plurality of applicators, is disposed to the body to be able to rotate, and arrange the mounted plurality of applicators in the working channel according to the rotation angle.

The invention claimed is:

1. A paranasal sinus entering endoscope, comprising:
a body, which comprises a plurality of operation parts;
an insertion part, which is extending from the front end of the body to be inserted into the paranasal sinus through the nasal cavity, and having at least one working channel; and
an applicator load part, which is disposed in the body and on which a plurality of applicators that are able to each selectively enter through one of the at least one working channel are able to be mounted,
wherein the plurality of operation parts comprise an operation unit for selecting one applicator of the plurality of applicators.

2. The paranasal sinus entering endoscope of claim 1, wherein the applicator load part allows any one of the plurality of applicators to be coaxially located with one of the at least one working channel.

3. The paranasal sinus entering endoscope of claim 1, wherein the operation unit a trigger structure to locate any one of the plurality of applicators to be adjacent to an inlet of one of the at least working channel by driving the applicator load part.

4. The paranasal sinus entering endoscope of claim 3, wherein the applicator load part allows the plurality of applicators to rotate around an axis of rotation about the applicator load part according to the operation of the operation unit.

5. The paranasal sinus entering endoscope of claim 1, wherein the insertion part comprises an image acquiring unit, which is disposed on the front end of the insertion part to acquire an image.

6. The paranasal sinus entering endoscope of claim 1, wherein the insertion part comprises:
 a rigid part, which is extending from the front end of the body; and
 a flexible part, which is extending from the rigid part and formed to be bent, and
 wherein the plurality of operation parts further comprise a bending operation part, which allows the flexible part to be bent by a user's operation.

7. The paranasal sinus entering endoscope of claim 1, wherein the plurality of applicators further comprise at least one among a guide wire, a balloon catheter, and a stent catheter.

8. An endoscope, comprising:
 a body, which comprises a plurality of operation parts;
 an insertion part, which is extending from the front end of the body to be inserted into the body of a patient, and having at least one working channel; and
 an applicator load part, which is configured to mount a plurality of applicators, is disposed to the body to be able to rotate,
 wherein the plurality of operation parts comprise an operation unit for selecting one applicator of the plurality of applicators by rotating the applicator load part.

* * * * *